US011309086B1

(12) United States Patent
Valliani et al.

(10) Patent No.: US 11,309,086 B1
(45) Date of Patent: Apr. 19, 2022

(54) METHODS AND SYSTEMS FOR INTERACTIVELY COUNSELING A USER WITH RESPECT TO SUPERVISED CONTENT

(71) Applicant: Safe Kids LLC, Vienna, VA (US)

(72) Inventors: Abbas Valliani, Vienna, VA (US); Zohran Valliani, Vienna, VA (US); Aahil Valliani, Vienna, VA (US)

(73) Assignee: Safe Kids LLC, Vienna, VA (US)

( * ) Notice: Subject to any disclaimer, the term of this patent is extended or adjusted under 35 U.S.C. 154(b) by 0 days.

(21) Appl. No.: 17/471,129

(22) Filed: Sep. 9, 2021

(51) Int. Cl.
| | |
|---|---|
| *G16H 50/20* | (2018.01) |
| *G16H 40/67* | (2018.01) |
| *G06Q 30/02* | (2012.01) |
| *G09B 5/02* | (2006.01) |
| *G06F 40/40* | (2020.01) |
| *G06F 3/0482* | (2013.01) |
| *A61B 5/00* | (2006.01) |
| *G16H 20/70* | (2018.01) |
| *G16H 10/20* | (2018.01) |
| *G16H 20/30* | (2018.01) |

(52) U.S. Cl.
CPC .......... *G16H 50/20* (2018.01); *G06F 3/0482* (2013.01); *G06F 40/40* (2020.01); *G06Q 30/0201* (2013.01); *G09B 5/02* (2013.01); *G16H 40/67* (2018.01); *A61B 5/4088* (2013.01); *G16H 10/20* (2018.01); *G16H 20/30* (2018.01); *G16H 20/70* (2018.01)

(58) Field of Classification Search
CPC ........ G16H 50/20; G16H 40/67; G16H 20/30; G16H 10/20; G16H 20/70; G06F 40/40; G06F 2/0482; G06Q 30/0201; A61B 5/4088

USPC ........................................................ 705/2–3
See application file for complete search history.

(56) References Cited

U.S. PATENT DOCUMENTS

| 8,655,717 | B2 * | 2/2014 | Schwarzberg | ..... G06Q 30/0207 705/14.1 |
|---|---|---|---|---|
| 10,949,774 | B1 | 3/2021 | Valliani | |
| 2014/0278513 | A1 * | 9/2014 | Prakash | ............. G06Q 30/0601 705/2 |

(Continued)

OTHER PUBLICATIONS

KR20160077800A (Google translation of KR20160077800A, published Jul. 4, 2016, 12 pages) (Year: 2016).

(Continued)

*Primary Examiner* — Michael Tomaszewski
(74) *Attorney, Agent, or Firm* — WEW IP Law PLLC

(57) ABSTRACT

The present disclosure is directed to interactively counseling a user with respect to supervised content. In particular, the methods and systems of the present disclosure may: determine, based at least in part on one or more machine learning (ML) models, that one or more interfaces displayed to a user include content of a content type designated by a content supervisor of the user for identification; and, responsive to determining that the interface(s) displayed to the user include content of the content type designated for identification, generate data representing a graphical user interface (GUI) for presentation to the user, the GUI indicating detection of the content of the content type and comprising interactive educational material counseling the user with respect to the content type.

18 Claims, 16 Drawing Sheets

(56) References Cited

U.S. PATENT DOCUMENTS

| | | | | |
|---|---|---|---|---|
| 2014/0372133 A1* | 12/2014 | Austrum | ................ | G16H 50/30 |
| | | | | 705/2 |
| 2016/0012194 A1* | 1/2016 | Prakash | ................ | G16H 40/40 |
| | | | | 705/2 |
| 2016/0082353 A1* | 3/2016 | Christovale | ........... | A63F 13/533 |
| | | | | 463/7 |
| 2017/0000422 A1* | 1/2017 | Moturu | ................ | A61B 5/0022 |
| 2017/0235912 A1* | 8/2017 | Moturu | ................. | G16H 40/67 |
| | | | | 705/2 |
| 2019/0387191 A1 | 12/2019 | Sharif-Ahmadi et al. | | |
| 2020/0253527 A1* | 8/2020 | Ellison | .................. | G16H 50/20 |

OTHER PUBLICATIONS

Wills (Exchanging Stories: Learning from Each Others Lived Experiences, 2011 4 pages) (Year: 2011).

\* cited by examiner

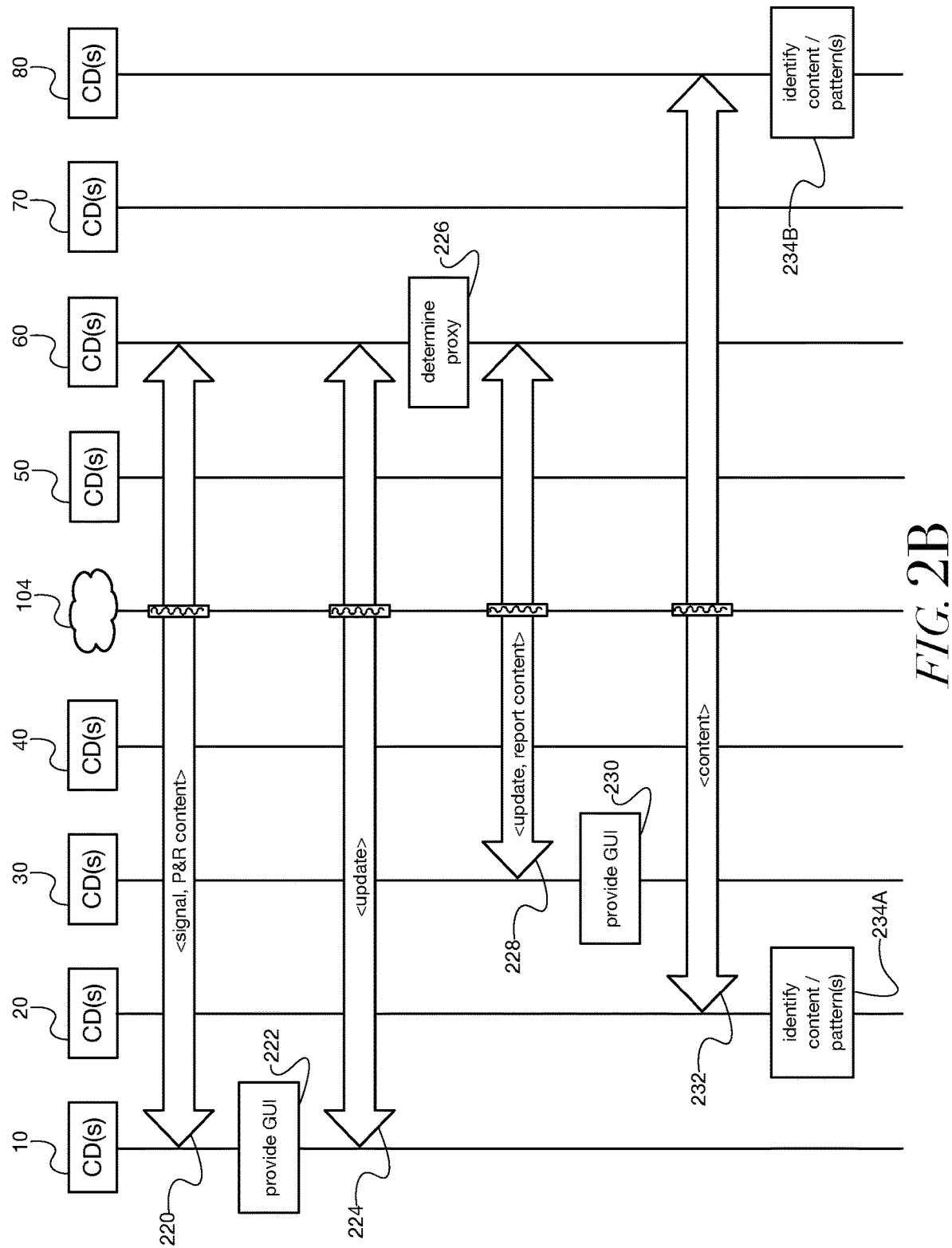

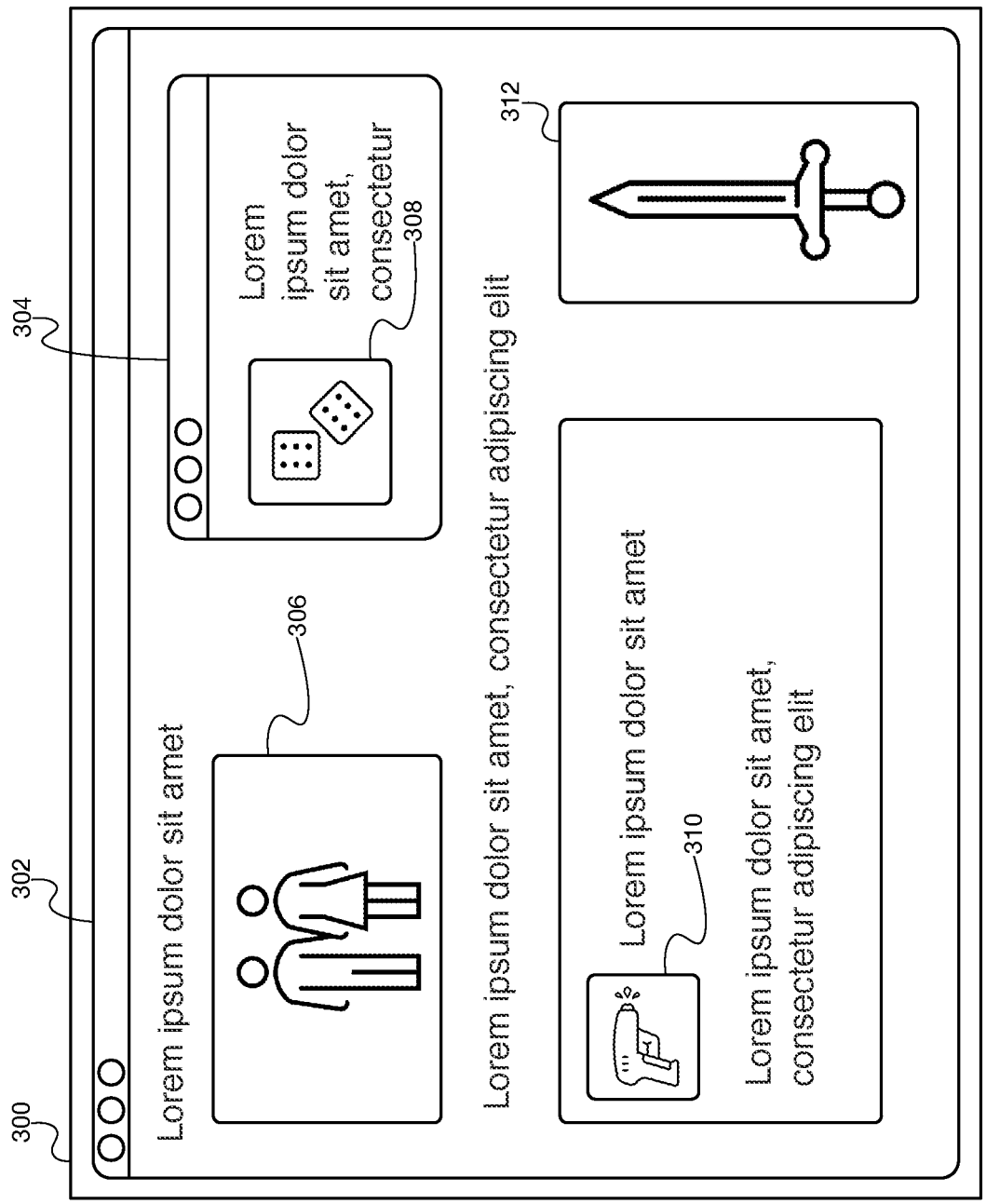

METHODS AND SYSTEMS FOR INTERACTIVELY COUNSELING A USER WITH RESPECT TO SUPERVISED CONTENT

FIELD

The present disclosure relates generally to content supervision. More particularly, the present disclosure relates to methods and systems for interactively counseling a user with respect to supervised content.

BACKGROUND

Computing devices (e.g., desktop computers, laptop computers, tablet computers, set-top devices, smartphones, wearable computing devices, and/or the like) are ubiquitous in modern society. They may support communications between their users, provide their users with entertainment, information about their environments, current events, the world at large, and/or the like. For certain users (e.g., children, employees, and/or the like) there may be a need and/or desire on the part of other individuals or organizations (e.g., parents, employers, and/or the like) to supervise, monitor, and/or the like content provided, displayed, and/or the like to the users by such devices.

SUMMARY

Aspects and advantages of embodiments of the present disclosure will be set forth in part in the following description, or may be learned from the description, or may be learned through practice of the embodiments.

One example aspect of the present disclosure is directed to a method. The method may include determining, by one or more computing devices and based at least in part on one or more machine learning (ML) models, that one or more interfaces displayed to a user include content of a content type designated by a content supervisor of the user for identification. The method may also include, responsive to determining that the interface(s) displayed to the user include content of the content type designated for identification, generating, by the computing device(s), data representing a graphical user interface (GUI) for presentation to the user, the GUI indicating detection of the content of the content type and comprising interactive educational material counseling the user with respect to the content type.

Another example aspect of the present disclosure is directed to a method that may include receiving, by one or more computing devices, data describing one or more activity patterns of a user with respect to at least one of the computing device(s). The method may also include receiving, by the computing device(s), data indicating one or more responses of the user to one or more prompts for objective information about at least one of their physical or mental health. The method may further include determining, by the computing device(s) and based at least in part on the data describing the activity pattern(s) of the user with respect to the at least one of the computing device(s), the data indicating the response(s) of the user to the prompt(s) for objective information about the at least one of their physical or mental health, and one or more ML models, a proxy of a subjective mental health state of the user.

A further example aspect of the present disclosure is directed to a method that may include identifying, by one or more computing devices, at least one designated activity pattern of a user with respect to at least one of the computing device(s). The method may also include, responsive to identifying the at least one designated activity pattern, generating, by the computing device(s) and based at least in part on one or more ML models and dialog input by the user regarding the identified designated activity pattern, one or more dialog responses responsive to the dialog input by the user and counseling the user to modify their behavior with respect to the identified activity pattern.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in this specification, which makes reference to the appended figures, in which:

FIGS. 2A-C depict an example event sequence according to example embodiments of the present disclosure;

FIGS. 3A-H and 4 depict example interfaces according to example embodiments of the present disclosure.

DETAILED DESCRIPTION

With reference now to the Figures, example embodiments of the present disclosure will be discussed in further detail.

Figure 1:
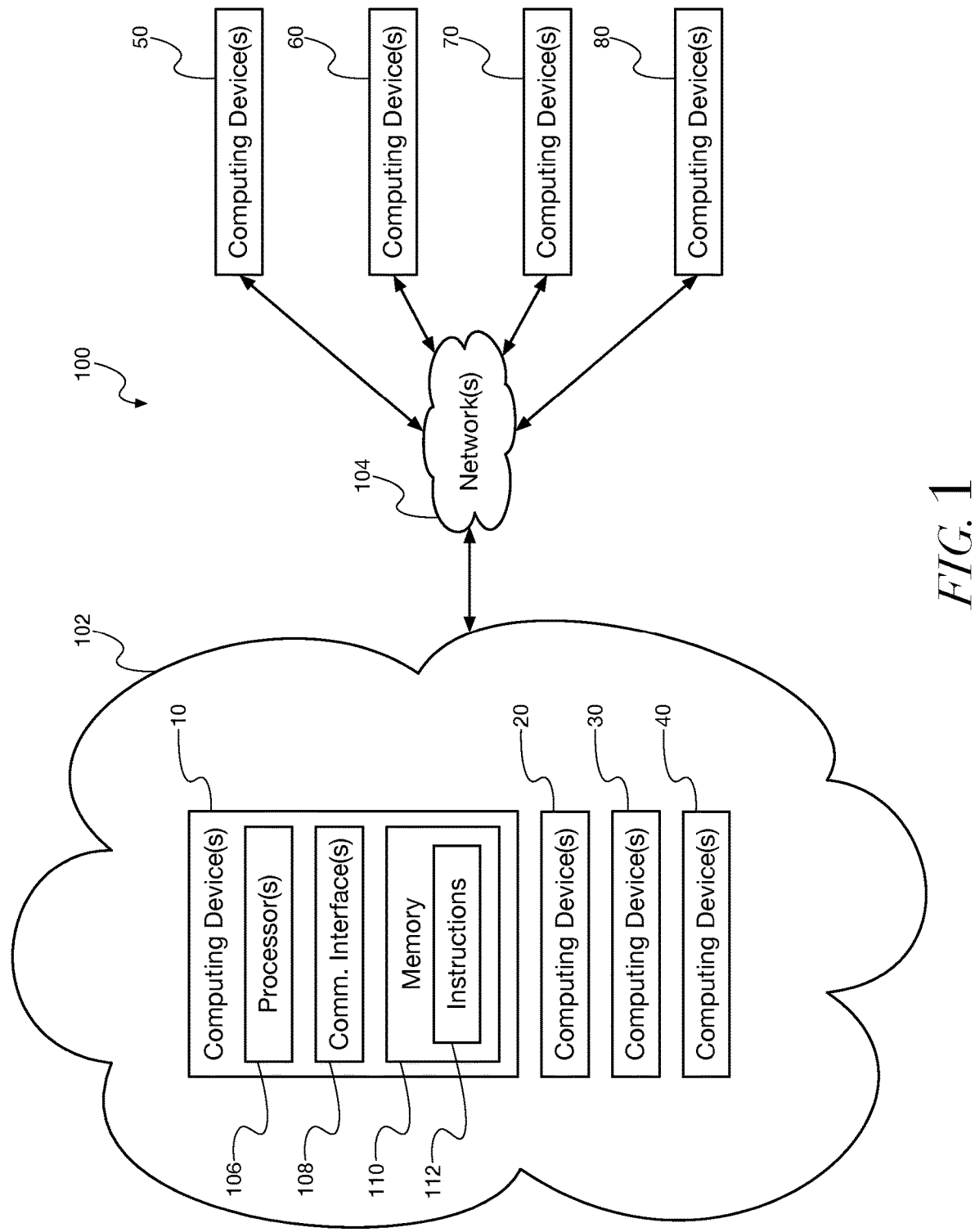
FIG. 1 depicts an example computing environment according to example embodiments of the present disclosure.

FIG. 1 depicts an example computing environment according to example embodiments of the present disclosure.

Referring to FIG. 1, environment 100 may include one or more computing devices (e.g., one or more desktop computers, laptop computers, set-top devices, tablet computers, mobile devices, smartphones, wearable devices, servers, and/or the like). For example, environment 100 may include computing devices 10, 20, 30, 40, 50, 60, 70, and/or 80, any one of which may include one or more associated and/or component computing devices (e.g., a mobile device and an associated wearable device, one or more associated servers, and/or the like). Environment 100 may also include one or more networks, for example, network(s) 102 and/or 104 (e.g., one or more wired networks, wireless networks, and/or the like). Network(s) 102 may interface computing device(s) 10, 20, 30, and/or 40, with one another and/or computing device(s) 50, 60, 70, and/or 80 (e.g., via network(s) 104, and/or the like).

Computing device(s) 10 may include one or more processor(s) 106, one or more communication interfaces 108, and memory 110 (e.g., one or more hardware components for storing executable instructions, data, and/or the like). Communication interface(s) 108 may enable computing device(s) 10 to communicate with computing device(s) 20, 30, 40, 50, 60, 70, and/or 80 (e.g., via network(s) 102, 104, and/or the like). Memory 110 may include (e.g., store, and/or the like) instructions 112. When executed by processor(s)

106, instructions 112 may cause computing device(s) 10 to perform one or more operations, functions, and/or the like described herein. It will be appreciated that computing device(s) 20, 30, 40, 50, 60, 70, and/or 80 may include one or more of the components described above with respect to computing device(s) 10.

Unless explicitly indicated otherwise, the operations, functions, and/or the like described herein may be performed by computing device(s) 10, 20, 30, 40, 50, 60, 70, and/or 80 (e.g., by computing device(s) 10, 20, 30, 40, 50, 60, 70, or 80, by any combination of one or more of computing device(s) 10, 20, 30, 40, 50, 60, 70, and/or 80, and/or the like).

Figure 2A:
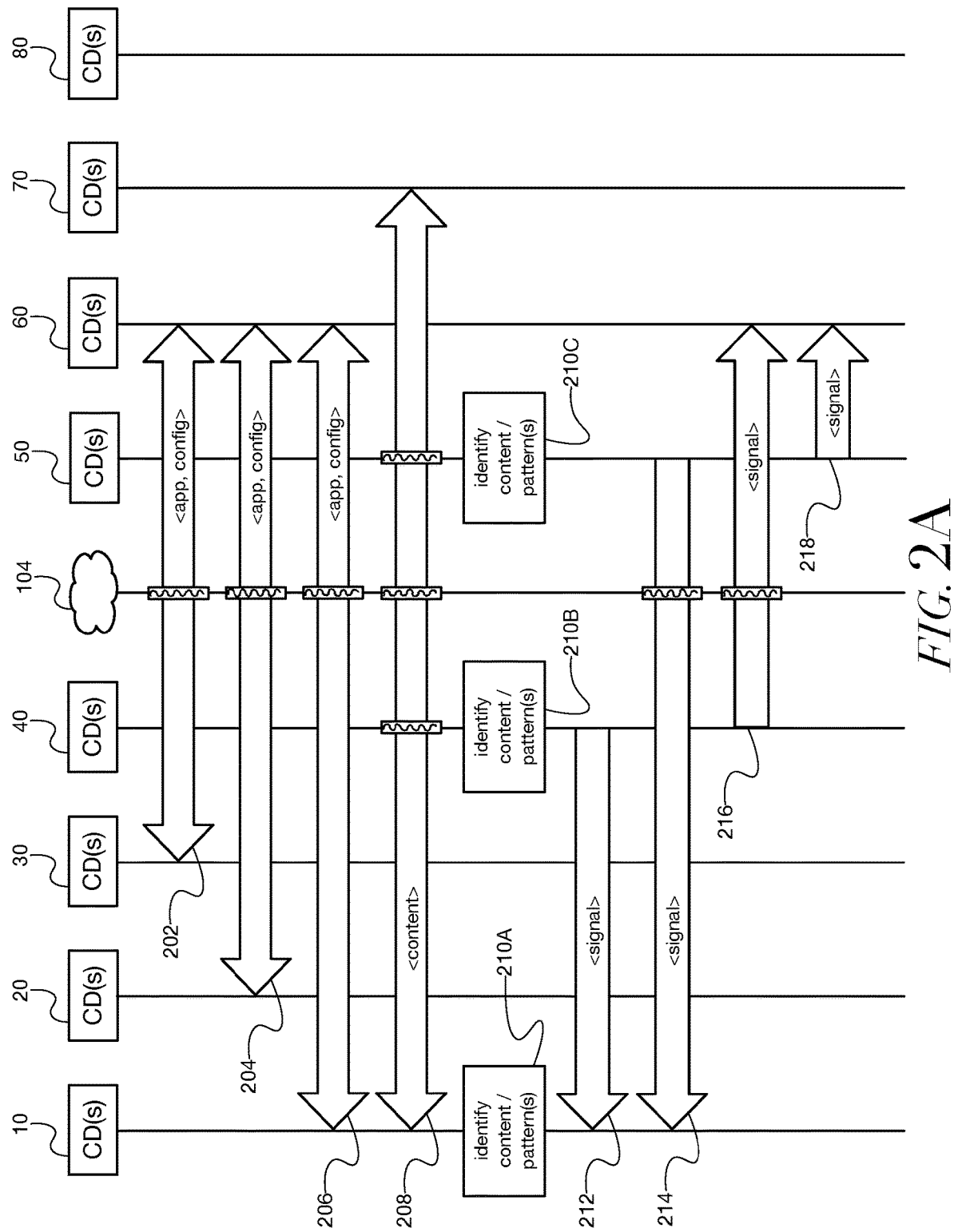
Figure 2C:
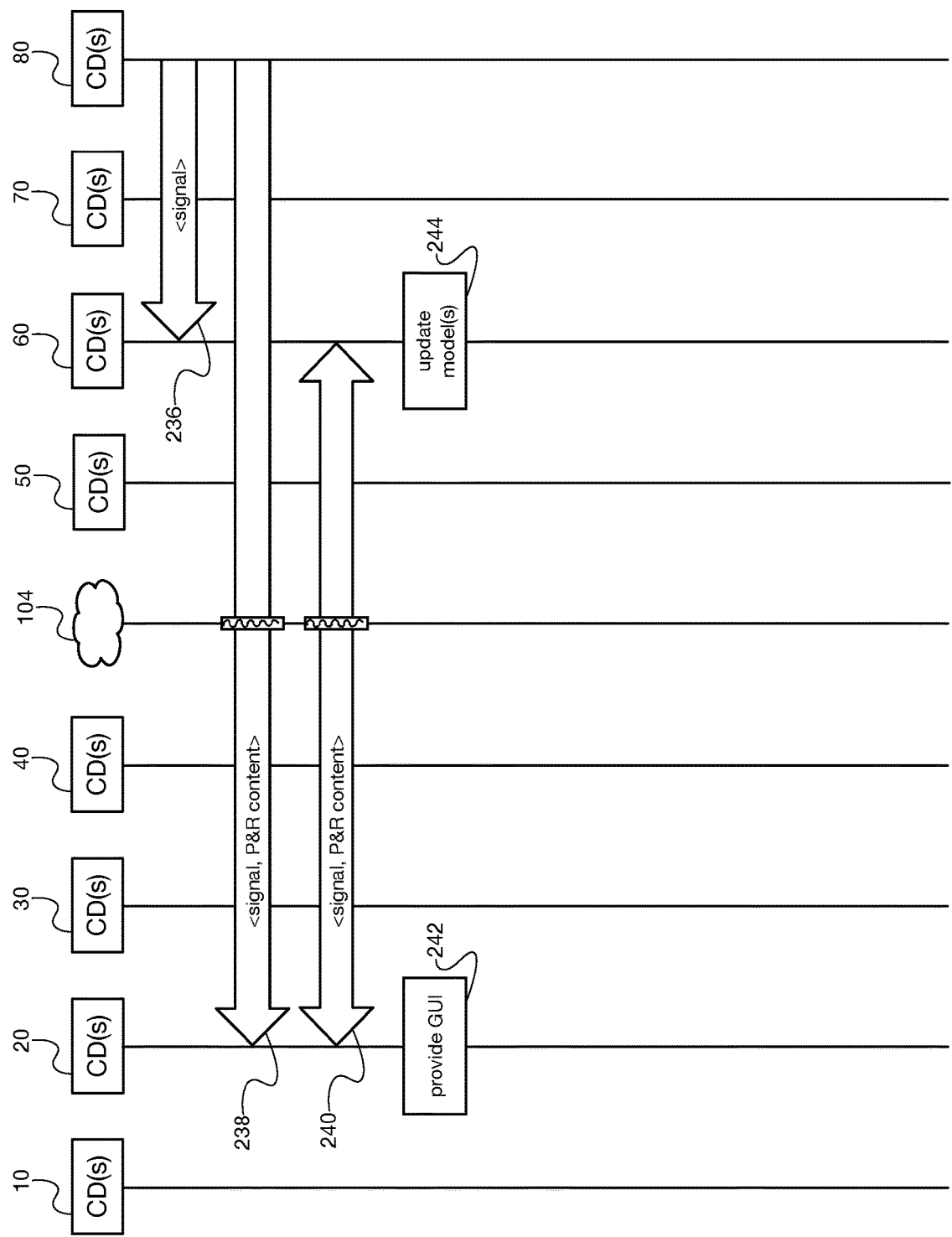

FIGS. 2A-C depict an example event sequence according to example embodiments of the present disclosure.

Referring to FIG. 2A, at (202), computing device(s) 30 (e.g., one or more user devices, and/or the like) and computing device(s) 60 (e.g., one or more servers, and/or the like) may communicate (e.g., via network(s) 104 (as indicated by the pattern-filled box over the line extending downward from network(s) 104), and/or the like) data registering one or more user devices, accounts, and/or the like for content supervision. For example, computing device(s) 10 and/or 20 may be utilized by one or more users (e.g., children, employees, and/or the like) of a user (e.g., parent, employer, and/or the like) utilizing computing device(s) 30, who may register such user device(s) and/or account(s) via a web, application, and/or the like interface provided by computing device(s) 60, and/or the like (e.g., by providing identifying information associated with such user device(s), account(s), and/or the like).

At (204), computing device(s) 20 and 60 may communicate data (e.g., one or more applications, configuration data, machine learning (ML) models, and/or the like), which computing device(s) 20 may receive, store, install, and/or the like. For example, a user (e.g., the parent, employer, and/or the like) may utilize computing device(s) 20 and/or 30 to download, install, and/or the like such data to computing device(s) 20 in order to supervise content displayed by computing device(s) 20, determine one or more activity patterns of the user(s) of computing device(s) 20, and/or the like.

Similarly, at (206), computing device(s) 10 and 60 may communicate data, which computing device(s) 10 may receive, store, install, and/or the like. For example, a user (e.g., the parent, employer, and/or the like) may utilize computing device(s) 10 and/or 30 to download, install, and/or the like such data to computing device(s) 10 in order to supervise content displayed by computing device(s) 10, determine one or more activity patterns of the user(s) of computing device(s) 10, and/or the like.

At (208), computing device(s) 10 and 70 (e.g., one or more website servers, content servers, and/or the like) may communicate data (e.g., content data, associated with one or more web browser sessions, application interfaces, and/or the like). Such data may be communicated via network(s) 102, 104, computing device(s) 40 (e.g., one or more local network devices associated with network(s) 102, and/or the like), and computing device(s) 50 (e.g., one or more network devices associated with an internet service provider (ISP) of network(s) 102, 104, and/or the like).

At (210), computing device(s) 10 (e.g., at (210A), and/or the like), 40 (e.g., at (210B), and/or the like), 50 (e.g., at (210C), and/or the like) may determine (e.g., identify, and/or the like) that one or more interfaces displayed to a user of computing device(s) 10 include content of a content type designated by a content supervisor (e.g., the user of computing device(s) 30, and/or the like) of the user for identification, one or more activity patterns of the user (e.g., with respect to computing device(s) 10, and/or the like) correspond to one or more activity patterns designated by the content supervisor of the user for identification, and/or the like.

In some embodiments, computing device(s) 10, 40, 50, and/or the like may determine that such interface(s) comprise imagery depicting violence, imagery associated with gambling, sexually explicit imagery, content associated with one or more of bullying, suicidal ideation, psychological concerns, and/or the like. In some of such embodiments, computing device(s) 10, 40, 50, and/or the like may determine (e.g., based at least in part on identifying such imagery, content, and/or the like) one or more activity patterns of the user correspond to one or more of the activity pattern(s) designated by the content supervisor. Additionally or alternatively, computing device(s) 10, 40, 50, and/or the like may determine one or more other activity patterns of the user correspond to one or more of the designated activity pattern(s), for example, one or more specified behaviors (e.g., online shopping, addictive behaviors, predatory communications, activity, such as searches, reading, browsing, and/or the like related to anxiety, family separation, death, divorce, eating disorders, and/or the like).

For example, referring to FIG. 3A, computing device(s) 10 may have displayed image 300. As illustrated, image 300 may depict interfaces 302 and 304 (e.g., associated with the web browser session(s), and/or the like). Interface 302 may include images 306, 310, and 312. Similarly, interface 304 may include image 308. Image 306 may comprise sexually explicit imagery, image 308 may comprise imagery associated with gambling, and images 310 and 312 may comprise imagery depicting violence, and/or the like.

In some embodiments, computing device(s) 10, 40, 50, and/or the like may determine that the interface(s) displayed to the user of computing device(s) 10 (e.g., interface(s) 302, 304, and/or the like) include content of the content type designated by the content supervisor, correspond to one or more of the designated activity pattern(s), and/or the like based at least in part on one or more machine learning (ML) models (e.g., one or more neural networks, and/or the like).

In some embodiments, computing device(s) 10, 40, 50, and/or the like may generate data representing one or more images (e.g., image 300, and/or the like) of the interface(s) displayed to the user of computing device(s) 10 (e.g., interface(s) 302, 304, and/or the like), and computing device(s) 10, 40, 50, and/or the like may determine that the interface(s) include the content of the content type, correspond to one or more of the designated activity pattern(s), and/or the like based at least in part on the data representing such image(s) of the interface(s). For example, computing device(s) 10, 40, 50, and/or the like may implement one or more aspects of the technology described in U.S. Pat. No. 10,949,774, issued Mar. 16, 2021, and entitled "METHODS AND SYSTEMS FOR SUPERVISING DISPLAYED CONTENT," the disclosure of which is incorporated herein by reference in its entirety.

Additionally or alternatively, computing device(s) 10, 40, 50, and/or the like may receive (e.g., from computing device(s) 10, and/or the like) peripheral input data (e.g., associated with keyboard input, mouse input, voice input, one or more search criteria, and/or the like) and/or network communication data (e.g., uniform resource locator (URL) requests for resolution, and/or the like) associated with activity of the user of computing device(s) 10 and may determine that the interface(s) include the content of the content type, correspond to one or more of the designated activity pattern(s), and/or the like based at least in part on such data, and/or the like. In some embodiments, computing device(s) 10, 40, 50, and/or the like may determine that the interface(s) include the content of the content type, correspond to one or more of the designated activity pattern(s), and/or the like based at least in part on employing one or more natural language processing (NLP) algorithms with respect to such data, and/or the like.

Returning to FIG. 2A, at (212), computing device(s) 40 may communicate (e.g., signal, and/or the like) data indicating identification of the content, activity pattern(s), and/or the like to computing device(s) 10, which may receive such data, and/or the like. Similarly, at (214), computing device(s) 50 may communicate (e.g., signal, and/or the like) data indicating identification of the content, activity pattern(s), and/or the like to computing device(s) 10, which may receive such data, and/or the like; at (216), computing device(s) 40 may communicate (e.g., signal, and/or the like) data indicating identification of the content, activity pattern(s), and/or the like to computing device(s) 60, which may receive such data, and/or the like; and, at (218), computing device(s) 50 may communicate (e.g., signal, and/or the like) data indicating identification of the content, activity pattern(s), and/or the like to computing device(s) 60, which may receive such data, and/or the like.

Referring to FIG. 2B, at (220), computing device(s) 10 and 60 may communicate (e.g., signal, and/or the like) data indicating identification of the content, activity pattern(s), and/or the like. Additionally or alternatively, computing device(s) 10 and 60 may communicate data comprising interactive educational material counseling the user of computing device(s) 10 with the respect to the identified content type, activity pattern(s), and/or the like (e.g., "P&R" or "pause and reflect" content, and/or the like).

At (222), responsive to determining that the interface(s) (e.g., interface(s) 302, 304, and/or the like) include content of the content type, correspond to one or more of the designated activity pattern(s), and/or the like, computing device(s) 10 may generate (e.g., based at least in part on the data communicated at (220), and/or the like) data representing a graphical user interface (GUI) for presentation (e.g., display, and/or the like) to the user of computing device(s) 10, and/or the like. Such a GUI may indicate identification, detection, and/or the like of the content of the content type, designated activity pattern(s), and/or the like. Additionally or alternatively, such a GUI may comprise interactive educational material counseling the user of computing device(s) 10 with respect to the identified content type, activity pattern(s), and/or the like. For example, the GUI may include interactive content counseling the user about the impact of viewing such content on their emotional health, wellbeing, productivity, and/or the like. Responsive to a determination that the interface(s) include content indicating a need for potential immediate intervention (e.g., suicidal ideation, self-harm thoughts, and/or the like), such a GUI may urge the user to defer action (e.g., via personal testimony from other individuals about their similar experiences, and/or the like).

Figure 3B:
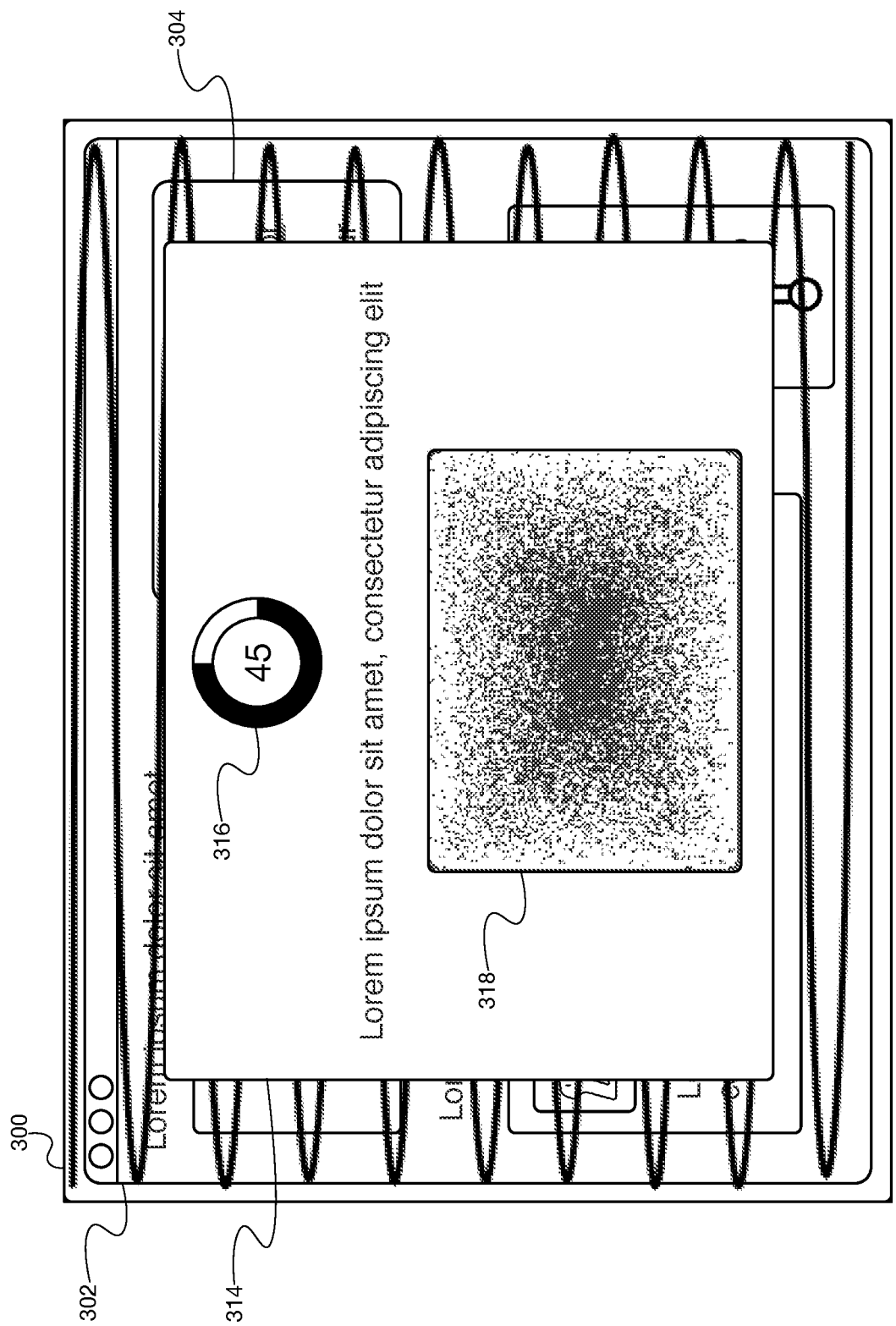

For example, referring to FIG. 3B, computing device(s) 10 may generate data representing interface 314, and/or the like. As illustrated, responsive to determining that the interface(s) (e.g., interface(s) 302, 304, and/or the like) include content of the content type, correspond to one or more of the designated activity pattern(s), and/or the like, computing device(s) 10 may restrict (e.g., via interface 314, and/or the like) access by the user of computing device(s) 10 to the interface(s) (e.g., interface(s) 302, 304, and/or the like) determined to include the content of the content type, correspond to one or more of the designated activity pattern(s), and/or the like.

In some embodiments, computing device(s) 10 may determine a time period for restricting such access by the user of computing device(s) 10 to the interface(s) (e.g., interface(s) 302, 304, and/or the like) determined to include the content of the content type, correspond to one or more of the designated activity pattern(s), and/or the like. In some of such embodiments, the GUI may include one or more elements (e.g., element(s) 316, and/or the like) indicating the time period, an elapsed portion of the time period, a remaining portion of the time period, and/or the like. In some embodiments, computing device(s) 10 may determine (e.g., dynamically, and/or the like) the time period based at least in part on the content type, activity pattern(s), a determined level of severity of the content of the content type, a determined number of times one or more interfaces displayed to the user of computing device(s) 10 included content of the content type, corresponded to one or more of the designated activity pattern(s), and/or the like.

In some embodiments, the interactive educational content counseling the user of computing device(s) 10 with respect to the content type, activity pattern(s), and/or the like may comprise a video (e.g., of an individual discussing their personal experience having viewed content of the content type, recovering from particular types of content addiction, anxiety, depression, violent urges, suicidal or self-harm thoughts, and/or the like). In some of such embodiments, the GUI may include one or more elements (e.g., element(s) 318, and/or the like) associated with such video, and/or the like.

Figure 3C:
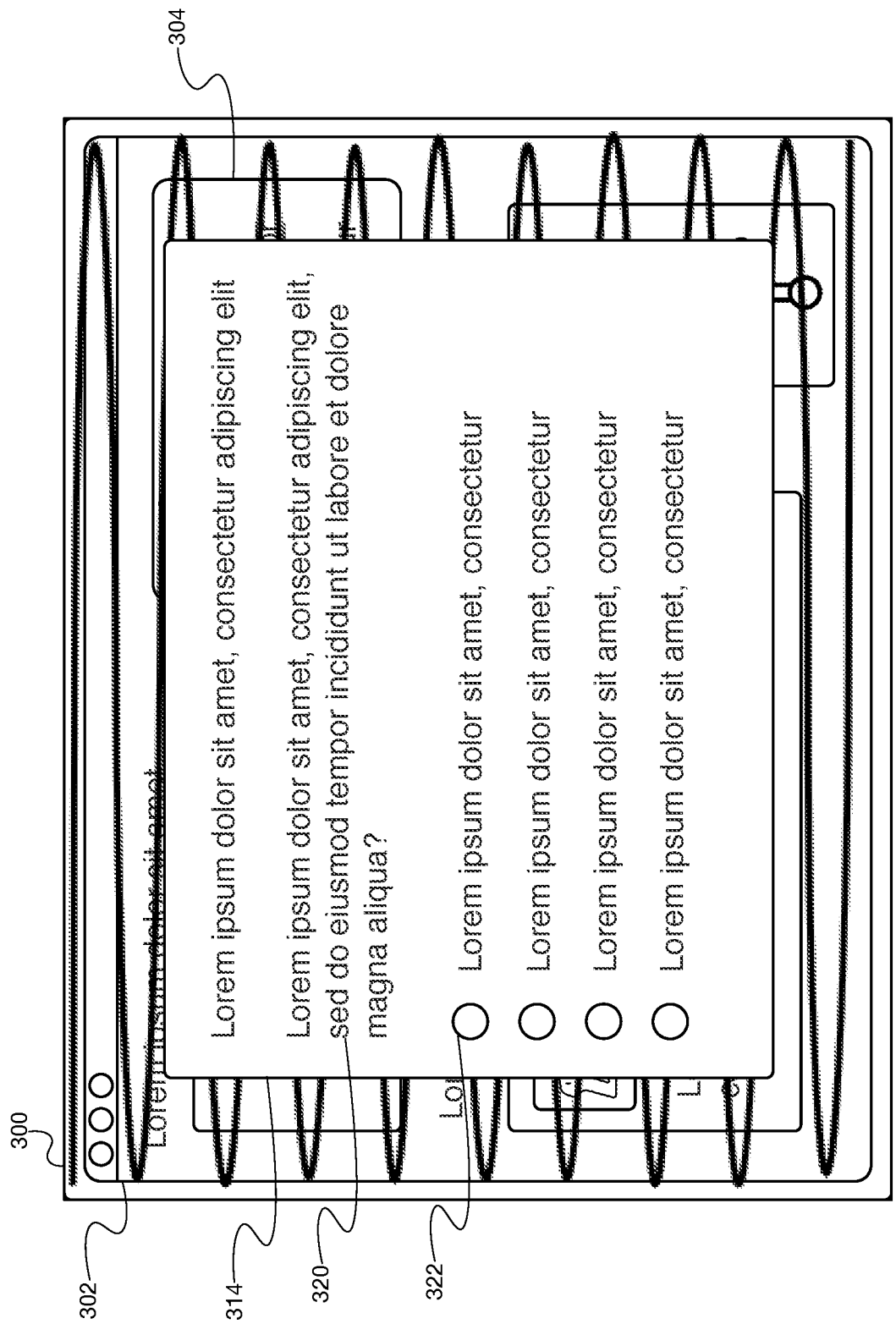

Additionally or alternatively, the GUI may comprise one or more interactive elements associated with the interactive educational content counseling the user of computing device(s) 10 with respect to the content of the content type, activity pattern(s), and/or the like. For example, referring to FIG. 3C, the GUI may provide the user of computing device(s) 10 with a quiz on one or more aspects of the interactive educational content (e.g., to reinforce desired behavior, asses their mood, emotional health, mental-state, and/or the like) and may include one or more associated elements, e.g., element(s) 320 (e.g., posing a question to the user of computing device(s) 10 regarding the interactive educational content, and/or the like) and/or element(s) 322 (e.g., presenting one or more possible responsive answers for selection by the user of computing device(s) 10, and/or the like).

Figure 3D:
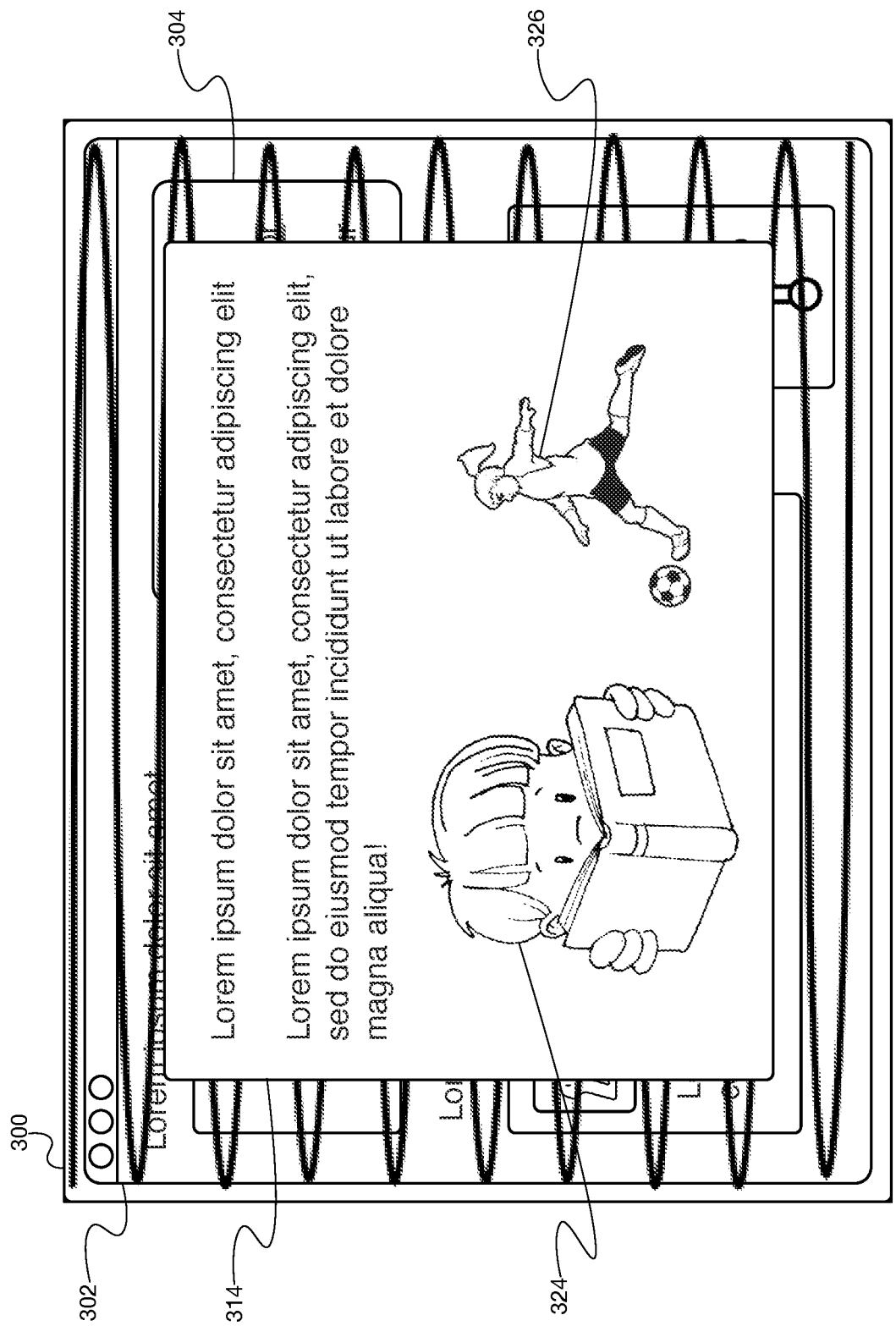

In some embodiments, the GUI may include one or more elements instructing the user of computing device(s) 10 to engage in a different computer activity, a non-computer activity, and/or the like for a determined period of time. For example, referring to FIG. 3D, the GUI may include element(s) 324 (e.g., instructing the user to engage in a different indoor, computer activity, and/or the like) and/or element(s) 326 (e.g., instructing the user to engage in an outdoor, non-computer activity, and/or the like).

Figure 3E:
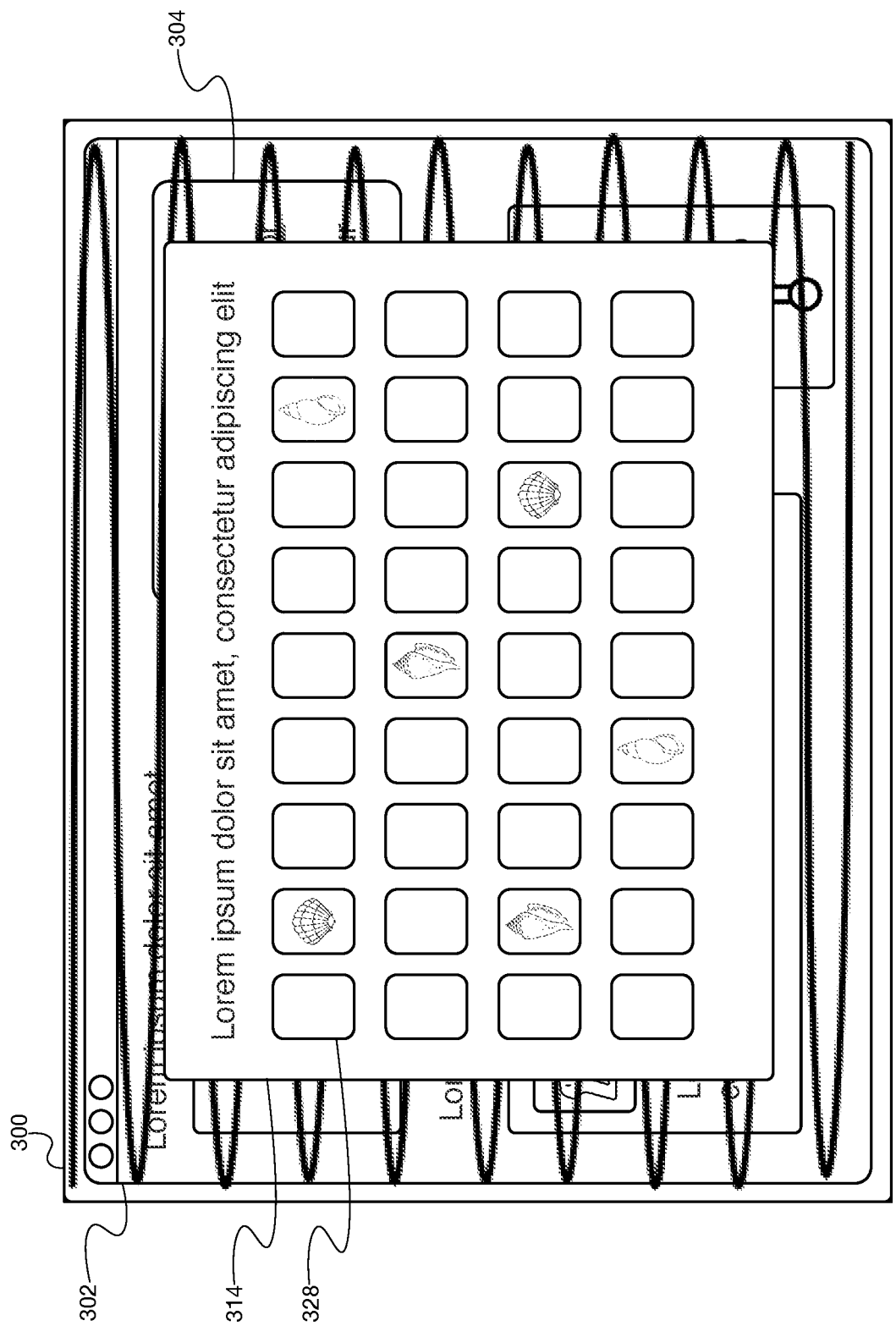

In some embodiments, the GUI may include interactive educational material comprising a game. For example, referring to FIG. 3E, the GUI may include element(s) 328 (e.g., corresponding to a memory recall game, and/or the like). In some of such embodiments, the game may be configured to assess cognitive decline, fatigue, and/or the like of the user of computing device(s) 10 (e.g., associated with viewing the content of the content type, exhibiting one or more of the designated activity pattern(s), and/or the like). Based at least in part on one or more interactions of the user of computing device(s) 10 with the game, a measure of such cognitive decline, fatigue, and/or the like may be determined (e.g., by computing device(s) 10, 60, and/or the like).

Figure 3F:
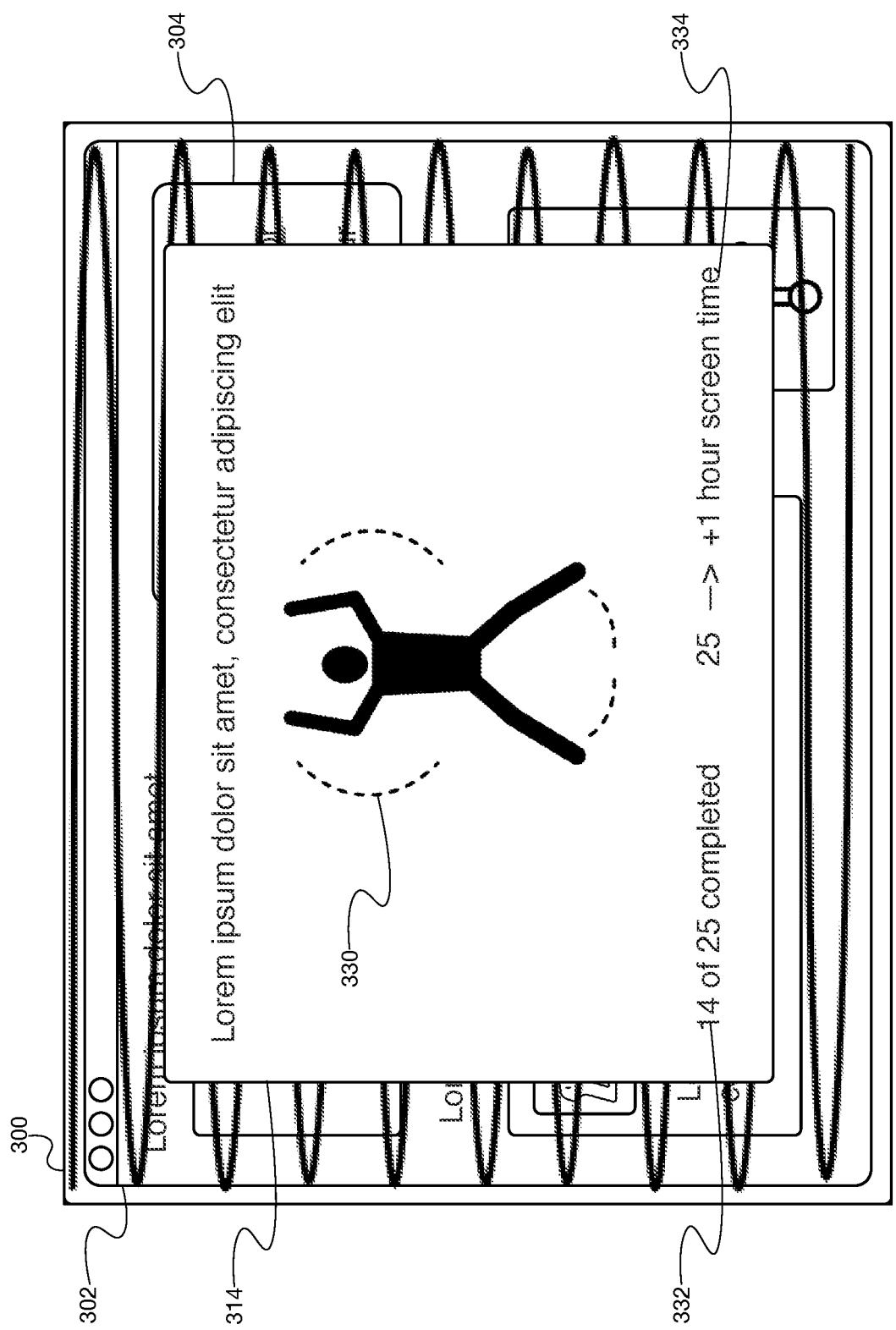

In some embodiments, the GUI may include interactive educational material comprising one or more prompts for the user of computing device(s) 10 to perform a specified physical exercise activity, and/or the like. For example, referring to FIG. 3F, the GUI may include element(s) 330 (e.g., prompting the user of computing device(s) 10 to perform jumping jacks, and/or the like). In some of such embodiments, a measure of the specified physical exercise activity performed by the user of computing device(s) 10 (e.g., in response to such prompt(s), and/or the like) may be determined (e.g., by computing device(s) 10, and/or the like). For example, in some embodiments, such a measure may be determined based at least in part on data generated by one or more sensors (e.g., cameras, wearable-device sensors, and/or the like) associated with computing device(s) 10, the user of computing device(s) 10, and/or the like. Additionally or alternatively, such a measure may be communicated to the user of computing device(s) 10 via the GUI, and/or the like. For example, the GUI may include element(s) 332 (e.g., indicating the number of jumping jacks performed by the user of computing device(s) 10 so far, to be performed in total, and/or the like).

In some embodiments, the GUI may include interactive educational material comprising one or more prompts for the user of computing device(s) 10 to modify their behavior with respect to viewing content of the content type, exhibiting the one or more of the designated activity pattern(s), and/or the like in exchange for an incentive, and/or the like. In some of such embodiments, the incentive may comprise an increase in a quota of a type of allowed interaction between the user of computing device(s) 10 and one or more of computing device(s) 10 over a defined period of time, and/or the like. For example, the GUI may include element(s) 334 (e.g., indicating an increase in allowed screen time for the user of computing device(s) 10 in exchange for the user of computing device(s) 10 completing the specified physical exercise activity, modifying their behavior with respect to viewing content of the content type, exhibiting the one or more of the designated activity pattern(s), and/or the like). Responsive to determining (e.g., based at least in part on the ML model(s), and/or the like) that the user of computing device(s) 10 modified their behavior (e.g., in accordance with the prompt(s), and/or the like) with respect to viewing content of the content type, exhibiting the one or more of the designated activity pattern(s), and/or the like, computing device(s) 10, and/or the like may increase such a quota (e.g., in accordance with the incentive, and/or the like).

Figure 3G:
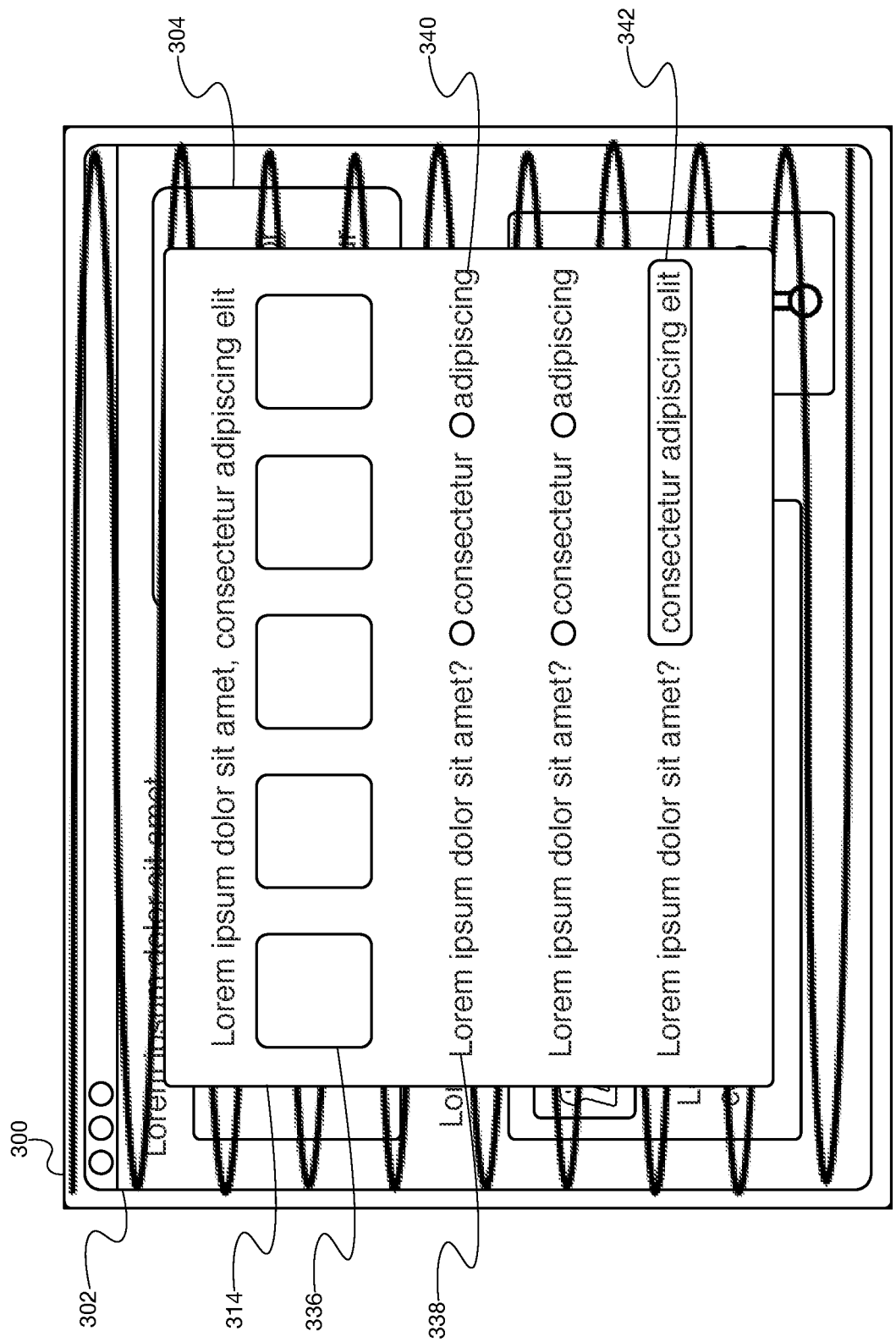

In some embodiments, the GUI may include interactive educational material comprising one or more prompts for the user of computing device(s) 10 to provide objective information about their physical health, mental health, and/or the like. For example, such prompt(s) may call for the user of computing device(s) 10 to provide responses indicating a level of nutrition, personal hygiene, sleep, physical activity, and/or the like within a specified timeframe (e.g., the past day, week, and/or the like). In some of such embodiments, the prompt(s) may call for the user of computing device(s) 10 to select one or more images (e.g., from a plurality of different images presented to the user of computing device(s) 10 in association with the prompt(s), and/or the like) as corresponding to the current state of their physical health, mental health, and/or the like. For example, referring to FIG. 3G, the GUI may include element(s) 336 (e.g., various images corresponding to different particular moods, and/or the like). Additionally or alternatively, the prompt(s) (e.g., element(s) 338, and/or the like) may call for the user of computing device(s) 10 to select one or more applicable responses from a discrete set of choices (e.g., element(s) 340, and/or the like), provide one or more freeform responses (e.g., via element(s) 342, and/or the like) to one or more open-ended questions for subsequent textual analysis, and/or the like.

Figure 3H:
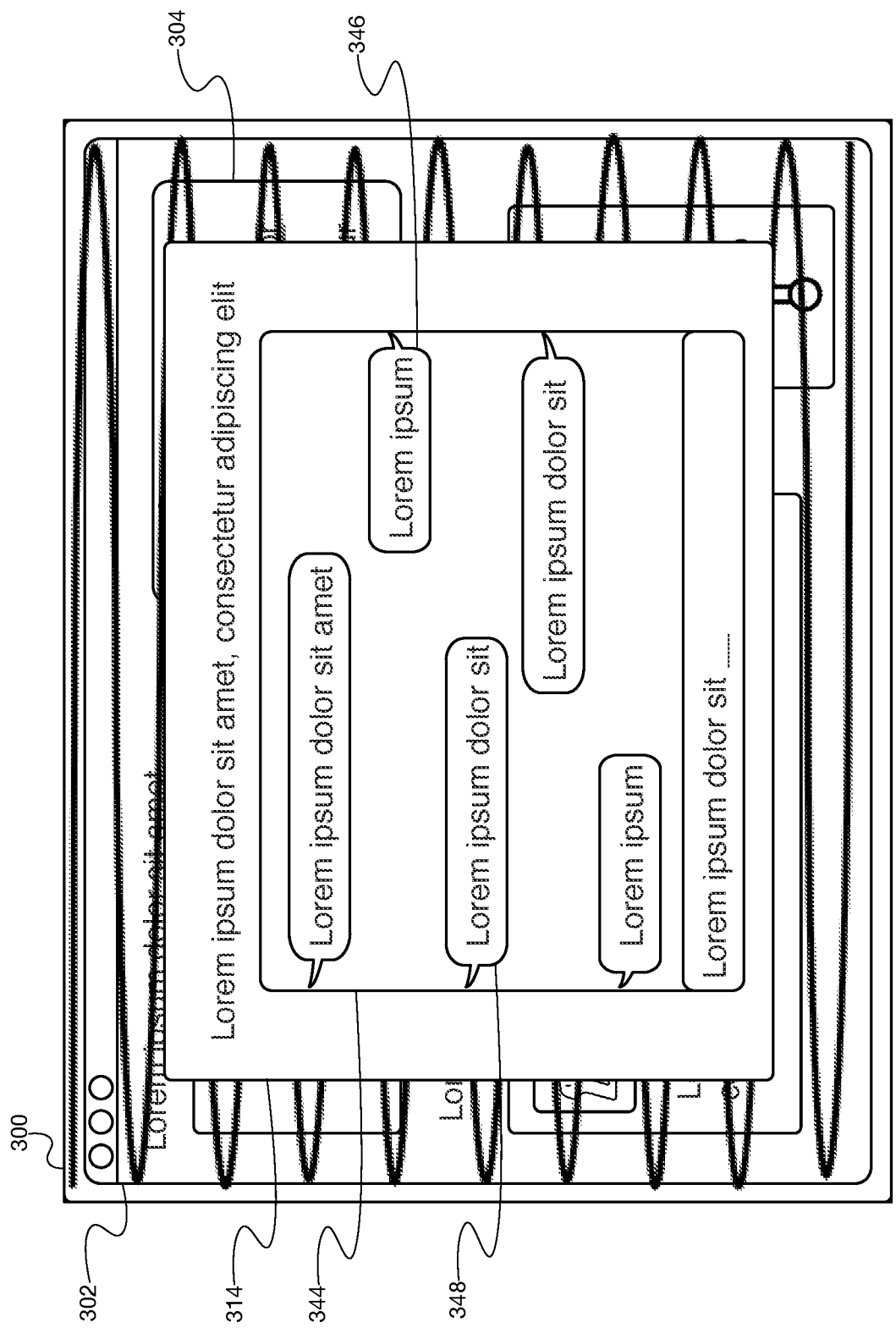

Referring to FIG. 3H, in some embodiments, the GUI may include interactive educational material comprising an automated dialog exchange (e.g., element(s) 344, and/or the like) with the user of computing device(s) 10 (e.g., a chatbot, and/or the like). For example, computing device(s) 10, and/or the like may generate, based at least in part on one or more ML models and/or dialog (e.g., element(s) 346, and/or the like) input by the user of computing device(s) 10 (e.g., regarding the content of the content type, the one or more of the designated activity pattern(s), and/or the like), one or more dialog responses (e.g., element(s) 348, and/or the like) responsive to the dialog (e.g., element(s) 346, and/or the like) input by the user of computing device(s) 10 (e.g., counseling the user of computing device(s) 10 to modify their behavior with respect to viewing content of the content type, exhibiting the one or more of the designated activity pattern(s), and/or the like). In some of such embodiments, one or more of the dialog response(s) may be generated based at least in part on dialog input (e.g., via computing device(s) 30, and/or the like) by the content supervisor of the user of computing device(s) 10 (e.g., in response to dialog generated as part of a counterpart automated dialog exchange with the content supervisor, and/or the like).

In some embodiments, responsive to the user of computing device(s) 10 interacting with the interactive educational material, computing device(s) 10 may close one or more elements of the GUI (e.g., element(s) 304, and/or the like) comprising the content of the content type, corresponding to the one or more of the designated activity pattern(s), and/or the like (e.g., such that the element(s) are no longer displayed to the user of computing device(s) 10, and/or the like).

Returning to FIG. 2B, at (224), computing device(s) 10 and 60 may communicate data (e.g., an update based at least in part on display of, user interaction with, and/or the like interface 314, and/or the like). For example, computing device(s) 10 may communicate to computing device(s) 60 data indicating, describing, identifying, generated based at least in part on, and/or the like the interface(s) determined to include content of the content type, corresponding to the one or more of the designated activity pattern(s), detection thereof, and/or the like, data indicating, describing, identifying, generated based at least in part on, and/or the like one or more interactions of the user of computing device(s) 10 (e.g., the response(s) to the prompt(s) for objective information about their physical health, mental health, and/or the like) with the interactive educational material, and/or the like, and computing device(s) 60 may receive such data, and/or the like.

At (226), computing device(s) 60 may determine a proxy (e.g., representative value, and/or the like) of the subjective mental health state of the user of computing device(s) 10, and/or the like. In some embodiments, computing device(s) 60 may determine such a proxy based at least in part on the data indicating, describing, identifying, generated based at least in part on, and/or the like the interface(s) determined to include the content of the content type, corresponding to the one or more of the designated activity pattern(s), the detection thereof, and/or the like, the data indicating, describing, identifying, generated based at least in part on, and/or the like the interaction(s) of the user of computing device(s) 10 (e.g., the response(s) to the prompt(s) for objective information about their physical health, mental health, and/or the like) with the interactive educational material, and/or the like. Additionally or alternatively, computing device(s) 60 may determine such a proxy based at least in part on one or more ML models. For example, in some embodiments, such ML model(s) may include at least one unsupervised ML model configured to determine such a proxy of the subjective mental health state of one or more users (e.g., the user of computing device(s) 10, and/or the like).

At (228), computing device(s) 30 and 60 may communicate data (e.g., an update, report, and/or the like based at least in part on display of, user interaction with, and/or the like interface 314, and/or the like). For example, computing device(s) 60 may communicate to computing device(s) 30 data indicating, describing, identifying, generated based at least in part on, and/or the like the interface(s) determined to include content of the content type, corresponding to the one or more of the designated activity pattern(s), detection thereof, and/or the like, data indicating, describing, identifying, generated based at least in part on, and/or the like one or more interactions of the user of computing device(s) 10 (e.g., the response(s) to the prompt(s) for objective information about their physical health, mental health, and/or the like) with the interactive educational material, and/or the like, data indicating, describing, identifying, generated based at least in part on, and/or the like the determined proxy of the subjective mental health state of the user of computing device(s) 10, and/or the like, and computing device(s) 30 may receive such data, and/or the like.

At (230), computing device(s) 30 may generate (e.g., based at least in part on the data communicated at (228), a portion thereof, and/or the like) data representing a GUI for presentation to the content supervisor. Such a GUI may indicate, for example, detection of the content (e.g., image(s) 306, 308, 310, 312, and/or the like) of the content type (e.g., determined to be included in interface(s) 302, 304, and/or the like), corresponding to the one or more of the designated activity pattern(s), and/or the like. Responsive to a determination that the interface(s) include content indicating a need for potential immediate intervention on the part of the content supervisor (e.g., suicidal ideation, self-harm thoughts, and/or the like), such a GUI may be presented to the content supervisor as soon as possible, technologically feasible, and/or the like.

Figure 4:
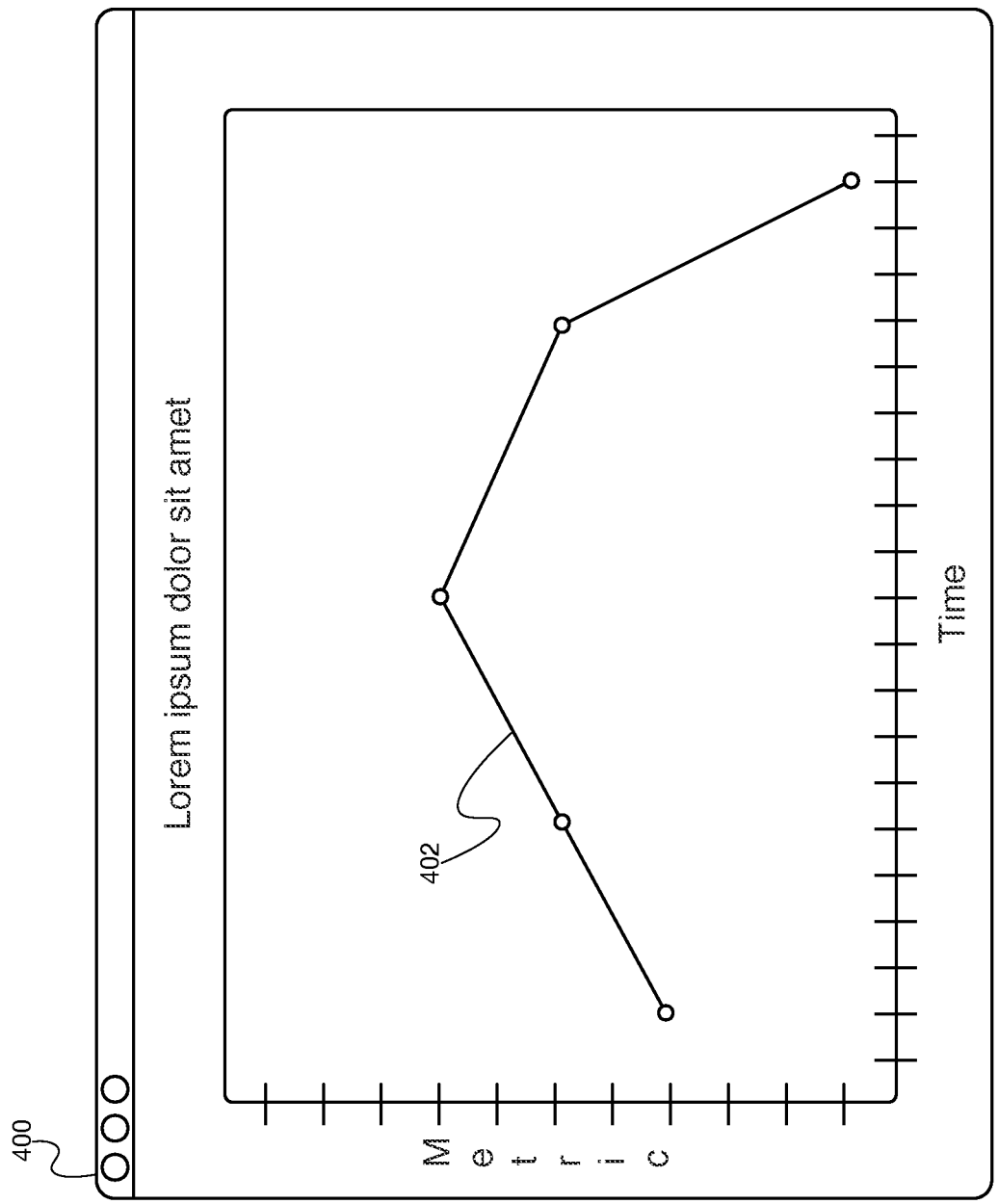

In some embodiments, the GUI for presentation to the content supervisor may comprise one or more elements graphically depicting activity of the user with respect to at least the content type, the one or more of the designated activity pattern(s), and/or the like, for example, based at least in part on a metric (e.g., the determined proxy of the subjective mental health state of the user of computing device(s) 10, a value based at least in part thereon, and/or the like) of mood, emotion, intent, mental health, productivity, age of the user, and/or the like, over a period of time including at least the time when the interface(s) determined to include the content of the content type, correspond to the one or more of the designated activity pattern(s), and/or the like were displayed (e.g., by computing device(s) 10, and/or the like). For example, referring to FIG. 4, computing device(s) 30 may generate data representing interface 400, which may include element(s) 402 depicting such a graph, and/or the like.

Returning to FIG. 2B, at (232), computing device(s) 20 and 80 (e.g., one or more website servers, content servers, and/or the like) may communicate data (e.g., content data, associated with one or more web browser sessions, application interfaces, social media, and/or the like).

At (234), computing device(s) 20 (e.g., at (234A), and/or the like) and/or 80 (e.g., at (234B), and/or the like) may determine (e.g., identify, and/or the like) that one or more interfaces displayed to a user of computing device(s) 20 (e.g., the same user previously referenced with respect to computing device(s) 10, a different user, and/or the like) include content of a content type designated by a content supervisor (e.g., the user of computing device(s) 30, and/or the like) of the user for identification, one or more activity patterns of the user (e.g., with respect to computing device(s) 20, and/or the like) correspond to one or more activity patterns designated by the content supervisor of the user for identification, and/or the like.

Referring to FIG. 2C, at (236), computing device(s) 80 may communicate (e.g., signal, and/or the like) data indicating identification of the content, activity pattern(s), and/or the like to computing device(s) 60, which may receive such data, and/or the like.

At (238), computing device(s) 80 may communicate (e.g., signal, and/or the like) data indicating identification of the content, activity pattern(s), and/or the like and comprising interactive educational material counseling the user of computing device(s) 20 with the respect to the identified content type, activity pattern(s), and/or the like to computing device(s) 20, which may receive such data, and/or the like. It will be appreciated that in certain contexts (e.g., social media, and/or the like) such an interactive counseling approach may present one or more advantages over other alternative approaches (e.g., suspending a user's account, and/or the like).

At (240), computing device(s) 20 and 60 may communicate (e.g., signal, and/or the like) data indicating identification of the content, activity pattern(s), and/or the like and comprising interactive educational material counseling the user of computing device(s) 20 with the respect to the identified content type, activity pattern(s), and/or the like.

At (242), responsive to determining that the interface(s) (e.g., interface(s) 302, 304, and/or the like) include content of the content type, correspond to one or more of the designated activity pattern(s), and/or the like, computing device(s) 20 may generate (e.g., based at least in part on the data communicated at (238), (240), and/or the like) data representing a GUI for presentation (e.g., display, and/or the like) to the user of computing device(s) 20, and/or the like. For example, referring to FIG. 3B, computing device(s) 20 may generate data representing interface 314, and/or the like.

At (244), computing device(s) 60 may update one or more ML models (e.g., based at least in part on the data communicated at (216), (218), (220), (224), (228), (236), (240), and/or the like). For example, as previously indicated, in some embodiments, the ML model(s) may include at least one unsupervised ML model configured to determine a proxy of the subjective mental health state of one or more users (e.g., the user(s) of computing device(s) 10, 20, and/or the like). In some of such embodiments, computing device(s) 60 may update one or more of such unsupervised ML model(s) based at least in part on one or more determined correlations between a determined proxy of the subjective mental health state of a user (e.g., the proxy determined at (226), and/or the like) and data (e.g., the data communicated at (236), (240), and/or the like) describing one or more subsequent interfaces displayed to the user, activity patterns of the user, and/or the like (e.g., with respect to computing device(s) 10, 20, and/or the like).

Figure 5:
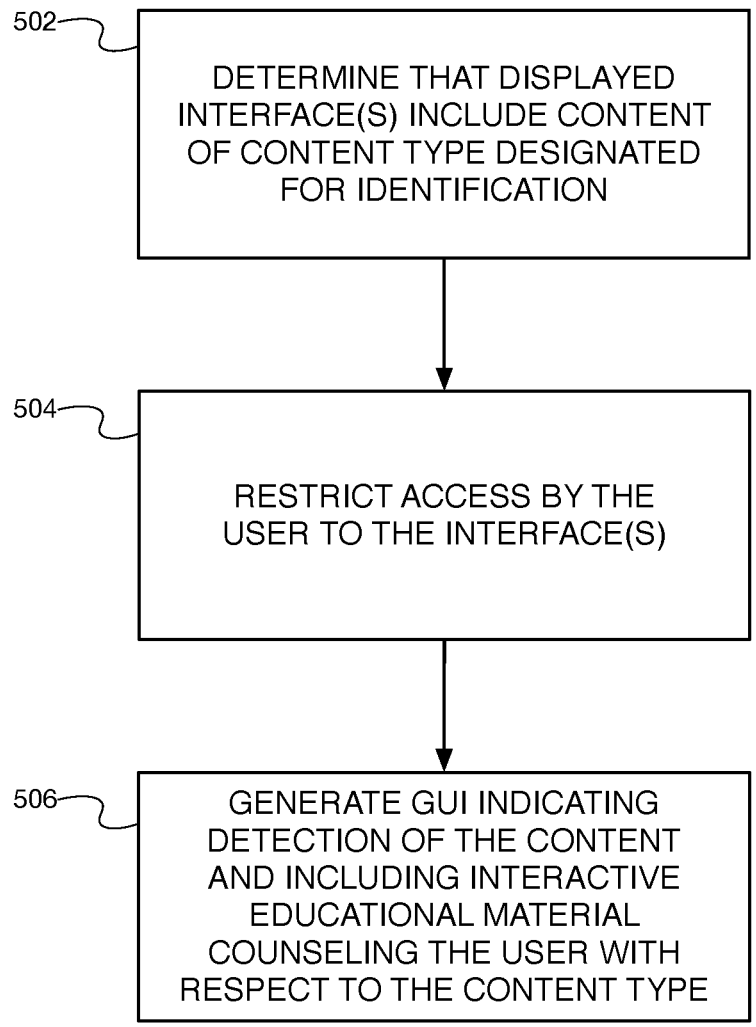
FIGS. 5-7 depict example methods according to example embodiments of the present disclosure.

FIG. 5 depicts an example method according to example embodiments of the present disclosure.

Referring to FIG. 5, at (502), one or more computing devices may determine that one or more interfaces displayed to a user include content of a content type designated by a content supervisor of the user for identification. For example, computing device(s) 10, 20, 40, 50, 80, and/or the like may determine that one or more interfaces (e.g., interface(s) 302, 304, and/or the like) displayed to a user of computing device(s) 10, 20, and/or the like include content of a content type designated (e.g., via computing device(s) 30, and/or the like) by a content supervisor of the user for identification, and/or the like.

At (504), responsive to determining that the interface(s) displayed to the user include content of the content type, the computing device(s) may restrict access by the user to the interface(s). For example, responsive to determining that interface(s) 302, 304, and/or the like include content of the content type(s) designated by the user of computing device(s) 30, and/or the like, computing device(s) 10, 20, and/or the like may restrict (e.g., via interface 314, and/or the like) access to interface(s) 302, 304, and/or the like.

At (506), responsive to determining that the interface(s) include content of the content type, the computing device(s) may generate data representing a GUI for presentation to the user. The GUI may indicate detection of the content of the content type, comprise interactive educational material counseling the user with respect to the content type, and/or the like. For example, responsive to determining that interface(s) 302, 304, and/or the like include content of a content type designated by the user of computing device(s) 30, and/or the like, computing device(s) 10, 20, and/or the like may generate interface 314 for presentation to the user of computing device(s) 10, 20, and/or the like.

Figure 6:
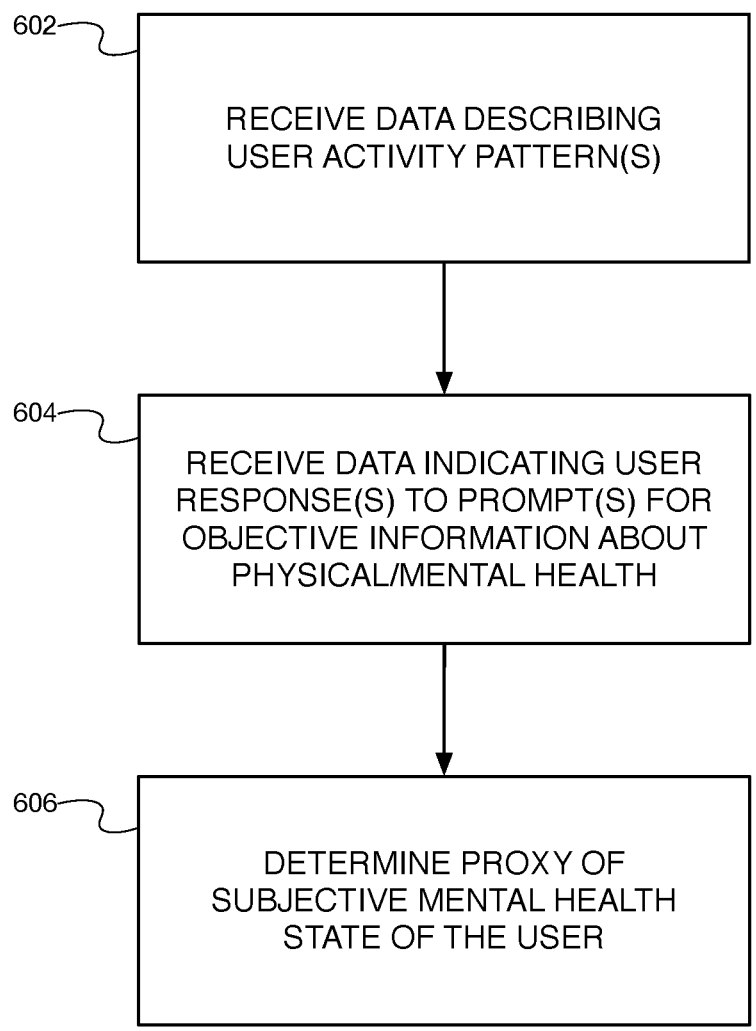

FIG. 6 depicts an additional example method according to example embodiments of the present disclosure.

Referring to FIG. 6, at (602), one or more computing devices may receive data describing one or more activity patterns of a user with respect to at least one of the computing device(s). For example, computing device(s) 60 may receive (e.g., at (216), (218), (220), (224), and/or the like) data describing one or more activity patterns of a user with respect to computing device(s) 10, and/or the like.

At (604), the computing device(s) may receive data indicating one or more responses of the user to one or more prompts for objective information about at least one of their physical or mental health. For example, computing device(s) 60 may receive (e.g., at (224), and/or the like) data indicating one or more responses of the user of computing device(s) 10 to one or more prompts for objective information about at least one of their physical or mental health, and/or the like.

At (606), the computing device(s) may determine (e.g., based at least in part on one or more ML models, the data received at (602), (604), and/or the like) a proxy of a subjective mental health state of the user. For example, computing device(s) 60 may determine (e.g., based at least in part on one or more ML models, the data received at (602), (604), and/or the like) a proxy of a subjective mental health state of the user of computing device(s) 10, and/or the like.

Figure 7:
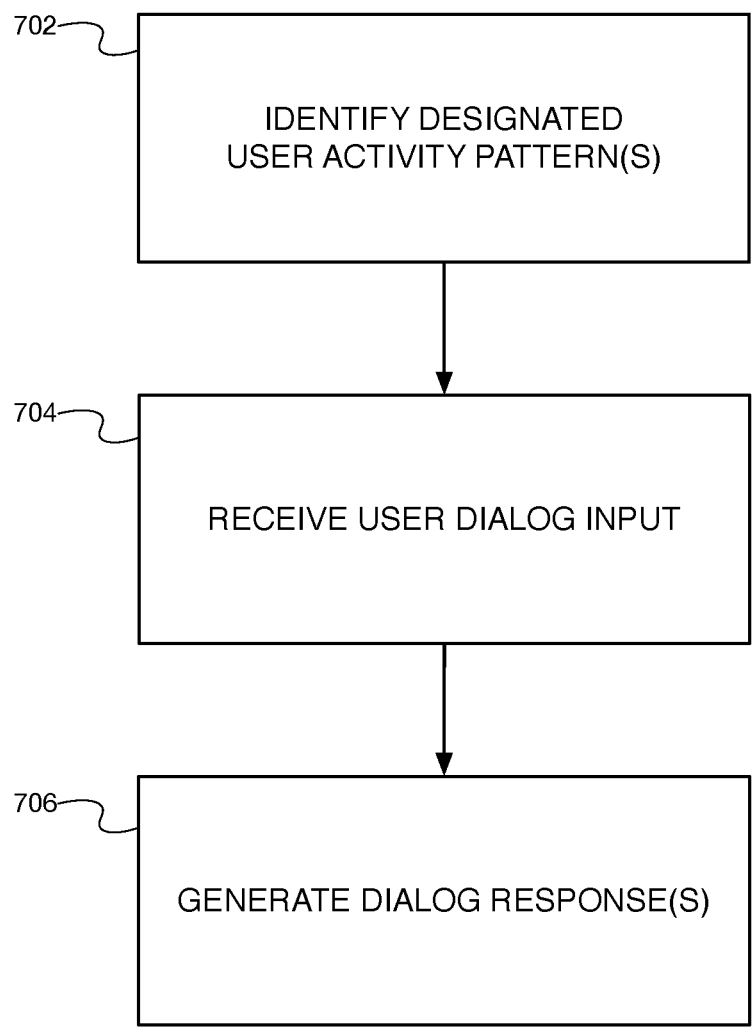

FIG. 7 depicts a further example method according to example embodiments of the present disclosure.

Referring to FIG. 7, at (702), one or more computing devices may identify at least one designated activity pattern of a user with respect to at least one of the computing device(s). For example, computing device(s) 10, 60, and/or the like may identify at least one designated activity pattern of a user with respect to at least one of computing device(s) 10, and/or the like.

At (704), the computing device(s) may receive dialog input by the user regarding the identified designated activity pattern(s). For example, computing device(s) 10, 60, and/or the like may receive dialog (e.g., element(s) 346, and/or the like) input by the user of computing device(s) 10, and/or the like.

At (706), the computing device(s) may generate (e.g., based at least in part on one or more ML models, the dialog input by the user regarding the identified designated activity pattern(s), and/or the like) one or more dialog responses responsive to the dialog input by the user and counseling the user to modify their behavior with respect to the identified designated activity pattern(s). For example, computing device(s) 10, 60, and/or the like may generate one or more dialog responses (e.g., element(s) 348, and/or the like) responsive to the input by the user of computing device(s) 10 and counseling the user of computing device(s) 10 to modify their behavior with respect to the identified designated activity pattern(s), and/or the like.

The technology discussed herein makes reference to servers, databases, software applications, and/or other computer-based systems, as well as actions taken and information sent to and/or from such systems. The inherent flexibility of computer-based systems allows for a great variety of possible configurations, combinations, and/or divisions of tasks and/or functionality between and/or among components. For instance, processes discussed herein may be implemented using a single device or component and/or multiple devices or components working in combination. Databases and/or applications may be implemented on a single system and/or distributed across multiple systems. Distributed components may operate sequentially and/or in parallel.

Various connections between elements are discussed in the above description. These connections are general and, unless specified otherwise, may be direct and/or indirect, wired and/or wireless. In this respect, the specification is not intended to be limiting.

The depicted and/or described steps are merely illustrative and may be omitted, combined, and/or performed in an order other than that depicted and/or described; the numbering of depicted steps is merely for ease of reference and does not imply any particular ordering is necessary or preferred.

The functions and/or steps described herein may be embodied in computer-usable data and/or computer-executable instructions, executed by one or more computers and/or other devices to perform one or more functions described herein. Generally, such data and/or instructions include routines, programs, objects, components, data structures, or the like that perform particular tasks and/or implement particular data types when executed by one or more processors of a computer and/or other data-processing device. The computer-executable instructions may be stored on a computer-readable medium such as a hard disk, optical disk, removable storage media, solid-state memory, read-only memory (ROM), random-access memory (RAM), or the like. As will be appreciated, the functionality of such instructions may be combined and/or distributed as desired. In addition, the functionality may be embodied in whole or in part in firmware and/or hardware equivalents, such as integrated circuits, application-specific integrated circuits (ASICs), field-programmable gate arrays (FPGAs), or the like. Particular data structures may be used to more effectively implement one or more aspects of the disclosure, and such data structures are contemplated to be within the scope of computer-executable instructions and/or computer-usable data described herein.

Although not required, one of ordinary skill in the art will appreciate that various aspects described herein may be embodied as a method, system, apparatus, and/or one or more computer-readable media storing computer-executable instructions. Accordingly, aspects may take the form of an entirely hardware embodiment, an entirely software embodiment, an entirely firmware embodiment, and/or an embodiment combining software, hardware, and/or firmware aspects in any combination.

As described herein, the various methods and acts may be operative across one or more computing devices and/or networks. The functionality may be distributed in any manner or may be located in a single computing device (e.g., server, client computer, user device, or the like).

Aspects of the disclosure have been described in terms of illustrative embodiments thereof. Numerous other embodiments, modifications, and/or variations within the scope and spirit of the appended claims may occur to persons of ordinary skill in the art from a review of this disclosure. For example, one of ordinary skill in the art may appreciate that the steps depicted and/or described may be performed in other than the recited order and/or that one or more illustrated steps may be optional and/or combined. Any and all features in the following claims may be combined and/or rearranged in any way possible.

While the present subject matter has been described in detail with respect to various specific example embodiments thereof, each example is provided by way of explanation, not limitation of the disclosure. Those skilled in the art, upon attaining an understanding of the foregoing, may readily produce alterations to, variations of, and/or equivalents to such embodiments. Accordingly, the subject disclosure does not preclude inclusion of such modifications, variations, and/or additions to the present subject matter as would be readily apparent to one of ordinary skill in the art. For instance, features illustrated and/or described as part of one embodiment may be used with another embodiment to yield a still further embodiment. Thus, it is intended that the present disclosure cover such alterations, variations, and/or equivalents.

What is claimed is:

1. A method comprising:
   determining, by one or more computing devices and based at least in part on one or more machine learning (ML) models, that one or more interfaces displayed to a user include content of a content type designated by a content supervisor of the user for identification;
   responsive to determining that the one or more interfaces displayed to the user include the content of the content type designated for identification, generating, by the one or more computing devices, data representing a graphical user interface (GUI) for presentation to the user, the GUI indicating detection of the content of the content type and comprising interactive educational material counseling the user with respect to the content type, the interactive educational material comprising a game configured to assess cognitive decline of the user associated with viewing the content of the content type; and
   determining, by the one or more computing devices and based at least in part on one or more interactions of the user with the game, a measure of cognitive decline of the user associated with viewing the content of the content type.

2. The method of claim 1, wherein the interactive educational material comprises one or more prompts for the user to perform a specified physical exercise activity.

3. The method of claim 2, comprising determining, by the one or more computing devices and based at least in part on data generated by one or more sensors associated with at least one of the user or the one or more computing devices, a measure of the specified physical exercise activity performed by the user in response to the one or more prompts.

4. The method of claim 1, wherein:
   the one or more interfaces displayed to the user comprise at least one interface associated with a web browser; and
   the method comprises, responsive to the user interacting with the interactive educational material, closing one or more elements of the at least one interface comprising the content of the content type such that the one or more elements comprising the content of the content type are no longer displayed to the user.

5. The method of claim 1, wherein the interactive educational material comprises one or more prompts for the user to modify their behavior with respect to viewing content of the content type in exchange for an incentive.

6. The method of claim 5, wherein:
   the incentive comprises an increase in a quota of a type of allowed interaction between the user and at least one of the one or more computing devices over a defined period of time; and
   the method comprises, responsive to determining, by the one or more computing devices and based at least in part on the one or more ML models, that the user modified their behavior with respect to viewing content of the content type in accordance with the one or more prompts, increasing, by the one or more computing devices, the quota in accordance with the incentive.

7. A method comprising:
   receiving, by one or more computing devices, data describing one or more activity patterns of a user with respect to at least one of the one or more computing devices;
   receiving, by the one or more computing devices, data indicating one or more responses of the user to one or more prompts for objective information about at least one of their physical or mental health;
   determining, by the one or more computing devices and based at least in part on the data describing the one or more activity patterns of the user with respect to the at least one of the one or more computing devices, the data indicating the one or more responses of the user to the one or more prompts for objective information about the at least one of their physical or mental health, and one or more unsupervised machine learning (ML) models, a proxy of a subjective mental health state of the user; and
   updating, by the one or more computing devices, the one or more unsupervised ML models based at least in part on one or more determined correlations between the proxy of the subjective mental health state of the user and data describing one or more subsequent activity patterns of the user with respect to at least one of the one or more computing devices.

8. The method of claim 7, wherein the one or more activity patterns of the user correspond to at least one of:
   online shopping;

one or more addictive behaviors;
viewing one or more of imagery depicting violence, imagery associated with gambling, or sexually explicit imagery; or
viewing content associated with one or more of bullying, suicidal ideation, or psychological concerns.

9. The method of claim 7, comprising identifying, by the one or more computing devices, the one or more activity patterns of the user based at least in part on one or more ML models and at least one of:
peripheral input data associated with activity of the user;
network communication data associated with activity of the user; or
one or more images of one or more interfaces displayed to the user.

10. The method of claim 7, wherein the data indicating the one or more responses of the user to the one or more prompts for objective information about the at least one of their physical or mental health indicates one or more images selected by the user, from amongst a plurality of different images presented to the user in association with the one or more prompts, as corresponding to a current state of the at least one of their physical or mental health.

11. The method of claim 7, wherein the data indicating the one or more responses of the user to the one or more prompts for objective information about the at least one of their physical or mental health indicates a level of at least one of nutrition, personal hygiene, sleep, or physical activity of the user within a timeframe specified by the one or more prompts.

12. The method of claim 7, comprising generating, by the one or more computing devices and based at least in part on the proxy of the subjective mental health state of the user, data representing a graphical user interface (GUI) for presentation to a content supervisor of the user.

13. A system comprising:
one or more processors; and
a memory storing instructions that when executed by the one or more processors cause the system to perform operations comprising:
determining, based at least in part on one or more machine learning (ML) models, that one or more interfaces displayed to a user include content of a content type designated by a content supervisor of the user for identification;
responsive to determining that the one or more interfaces displayed to the user include the content of the content type designated for identification, generating data representing a graphical user interface (GUI) for presentation to the user, the GUI indicating detection of the content of the content type and comprising interactive educational material counseling the user with respect to the content type, the interactive educational material comprising a game configured to assess cognitive decline of the user associated with viewing the content of the content type; and
determining, based at least in part on one or more interactions of the user with the game, a measure of cognitive decline of the user associated with viewing the content of the content type.

14. The system of claim 13, wherein the interactive educational material comprises one or more prompts for the user to perform a specified physical exercise activity.

15. The system of claim 14, wherein the operations comprise determining, based at least in part on data generated by one or more sensors associated with at least one of the user or the system, a measure of the specified physical exercise activity performed by the user in response to the one or more prompts.

16. The system of claim 13, wherein:
the one or more interfaces displayed to the user comprise at least one interface associated with a web browser; and
the operations comprise, responsive to the user interacting with the interactive educational material, closing one or more elements of the at least one interface comprising the content of the content type such that the one or more elements comprising the content of the content type are no longer displayed to the user.

17. The system of claim 13, wherein the interactive educational material comprises one or more prompts for the user to modify their behavior with respect to viewing content of the content type in exchange for an incentive.

18. The system of claim 17, wherein:
the incentive comprises an increase in a quota of a type of allowed interaction between the user and the system over a defined period of time; and
the operations comprise, responsive to determining, based at least in part on the one or more ML models, that the user modified their behavior with respect to viewing content of the content type in accordance with the one or more prompts, increasing the quota in accordance with the incentive.

* * * * *